(12) United States Patent
Tanaka et al.

(10) Patent No.: US 7,154,028 B2
(45) Date of Patent: Dec. 26, 2006

(54) GIBBERELLIN 2-OXIDASE GENE, FUNCTIONS AND USES THEREOF

(75) Inventors: Hiroshi Tanaka, Ibaraki (JP); Toshiaki Kayano, Ibaraki (JP); Makoto Matsuoka, Aichi (JP); Masatomo Kobayashi, Ibaraki (JP); Tamio Saito, Ibaraki (JP); Tomoaki Sakamoto, Tokyo (JP); Miho Sakai, Ohita (JP)

(73) Assignee: National Agriculture and Bio-Oriented Research Organization, Ibaraki (JP)

( * ) Notice: Subject to any disclaimer, the term of this patent is extended or adjusted under 35 U.S.C. 154(b) by 211 days.

(21) Appl. No.: 10/392,325

(22) Filed: Mar. 18, 2003

(65) Prior Publication Data

US 2004/0060080 A1  Mar. 25, 2004

(30) Foreign Application Priority Data

Sep. 20, 2002  (JP) ............................. 2002-276051

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. .................... 800/298; 800/278; 800/290; 435/419; 435/320.1; 536/23.1; 536/23.6

(58) Field of Classification Search ............... 536/23.1, 536/23.6; 435/320.1, 419, 468; 800/278, 800/298, 290
See application file for complete search history.

(56) References Cited

U.S. PATENT DOCUMENTS 6,451,581 B1 * 9/2002 Falco et al. ............... 435/252.3
6,677,502 B1 * 1/2004 Allen et al. ................ 800/278

FOREIGN PATENT DOCUMENTS

JP    2001-238686 A      9/2001
WO    WO 99/66029   *   12/1999
WO    WO 01/48215 A1    7/2001

OTHER PUBLICATIONS

Sakai, M. et al. "Control of the endogenous gibberellin content by rice gibberellin 2-oxidase" The 2002 Annual Meeting and the 42nd Symposium of the Japanese Society of Plan Physiologists.

Graebe, J. E. "Gibberellin biosynthesis and control." *Ann. Rev. Plant. Physiol.* 1987; 38:419-65.

Hedden, P. et al. "Gibberellin biosynthesis: enzymes, genes and their regulation." *Annu. Rev. Plant Physiol. Plant Mol. Biol.*, 1997; 48:431-60.

Hooley, R. "Gibberellins: perception, transduction and responses." *Plant Molecular Biology.* 1994; 26:1529-55.

Kobayashi, M., et al. "Quantitative analysis of endogenous gibberellins in normal and dwarf cultivars of rice." *Plant Cell Physiol.* 1989; 30(7):963-9.

Lange, T. "Molecular biology of gibberellin synthesis." *Planta,* 1998; 204:409-19.

Lester, D. R., et al. "Gibberellin 2-oxidation and the *SLN* gene of *Pisum sativum.*" *The Plant Journal.* 1999; 19(1):65-73.

Martin, D. N., et al. "The *SLENDER* gene of pea encodes a gibberellin 2-oxidase." *Plant Physiol.* 1999; 121:775-81.

Ross, J. J., et al. "Genetic regulation of gibberellin deactivation in *Pisum.*" *The Plant Journal* 1995, 7(3): 513-23.

Sakamoto, T., et al. "Expression of a gibberellin 2-oxidase gene around the shoot apex is related to phase transition in rice." *Plant Physiol.* 2001; 125:1508-16.

Thomas, S. G., et al. "Molecular cloning and functional espression of gibberellin 2-oxidases, multifunctional enzymes involved in gibberellin deactivation." *Proc. Natl. Acad. Sci. USA.* 1999; 96:4698-703.

* cited by examiner

*Primary Examiner*—Stuart F. Baum
(74) *Attorney, Agent, or Firm*—Lahive & Cockfield, LLP; Elizabeth A. Hanley, Esq.; Jeanne M. DiGiorgio, Esq.

(57) ABSTRACT

An objective of the present invention is to provide DNAs encoding novel plant proteins having a gibberellin (GA) 2-oxidation activity. Another objective is to modify plant height by utilizing these DNAs for regulating the gibberellin content.

PCR was performed using degenerate primers, and novel OsGA2ox2 and OsGA2ox3 genes were obtained. The present inventors discovered that unlike products of other GA2-oxidases such as OsGA2ox1, the product of OsGA2ox3 catalyzes the two-step oxidation of $GA_{20}$ to $GA_{29}$ and then of $GA_{29}$ to $GA_{29}$-catabolite. In addition, the present inventors also found that the growth of the transgenic rice plants expressing OsGA2ox3 was suppressed as compared to control plants.

17 Claims, 6 Drawing Sheets

FIG. 1

| | | | |
|---|---|---|---|
| OsGA2ox1 | 1 | MVVPSATTP--ARQETVVAAAPPAAAASGVVGGGGVTIATVDMS--AERGAVARQVATA | 56 |
| OsGA2ox2 | 1 | ----AAAECG-R----------AVFCRRR-VVP----AP-G--ELS-----R | 55 |
| OsGA2ox3 | 1 | ---LGP-AVDHI-PLL--RS---DPG---DVFS----PV--LGSP----A--A--VD | 45 |
| OsGA2ox1 | 57 | CAAHGFFRCVGHGVPAAAPVAARLDAATAAFFAMAPAEKQRAGPASPLGYGCRSI-GFNGD | 116 |
| OsGA2ox2 | 56 | --GS--A-N---PR-S-AM-GA--R-G----L-PD-----S--A---- | 113 |
| OsGA2ox3 | 46 | --ERY--KV-N--TDTM-DKAESEAVR--SQTQPD-D-S--Y-F--SKR- | 103 |
| OsGA2ox1 | 117 | VGELEYLLLHANPAAVAHRART--------D------AMD-P-SR-F---S-----A-IVNEY | 154 |
| OsGA2ox2 | 114 | -I-----S-D--RK-SA--DRE--PRRFRYAI-HAAYA-N--NR-RITL-RSQV--D | 173 |
| OsGA2ox3 | 104 | M-W-------L-L-DD--SL--A--A----CTVPSCA--V---RA---AL-- | 138 |
| OsGA2ox1 | 155 | EAMKKLACEI-LDLLGEGEGL-KDPRYFSKLTTNADSDCLLRI-NHYPPSCNIHK-DHDDQC | 214 |
| OsGA2ox2 | 174 | V--VRQ--HV----R--TSLTR-I-AT-N-S-I------A--A-AAG-H- | 229 |
| OsGA2ox3 | 139 | SGVR-V-VRVMEAMS--I-AQADAL-AI-V-AEG-QVF-V----I---RA-QGLG- | 194 |
| OsGA2ox1 | 215 | NI-KSLVSTKASNGGNLMAGGR-GFGEHSDPQILSLLRANDVEGLQVFVPD--HEGKEMWV | 272 |
| OsGA2ox2 | 230 | --------G--P-APTAA------------V---AD----LL--AAAA-DSV---- | 279 |
| OsGA2ox3 | 195 | -----------------T------LV-V-S-GTS---I-ALR----------Q-- | 229 |
| OsGA2ox1 | 273 | QVPSDPSAI-FVNVGDVLQAIL-TNGRLI-SI-RHRVI-ATACRPRLSTI-YFASPPLHARI-SALPE | 332 |
| OsGA2ox2 | 280 | P--P------F-----L-----V-------VVGTGK-----A------- | 339 |
| OsGA2ox3 | 230 | S--RDSF----S----V---FK--VK-VNSLKS-V-F--GG----AP--Q | 289 |
| OsGA2ox1 | 333 | TI-TASSPRRYRSFTWAEYKTTMYSLRLSHSRLELFKI-DDDDSDNA-S--EGKA | 382 (SEQ ID NO:5) |
| OsGA2ox2 | 340 | VA-GA-A------R-T-N--D-HAG-G-G-AGVGDDDDHE | 392 (SEQ ID NO:2) |
| OsGA2ox3 | 290 | LLGEGEQSL-KE---D-----KAAL-KS-GDN-AQ-------E----K | 327 (SEQ ID NO:4) |

SEQUENCE LISTING

<160> NUMBER OF SEQ ID NOS: 7

<210> SEQ ID NO 1
<211> LENGTH: 1179
<212> TYPE: DNA
<213> ORGANISM: Oryza sativa
<220> FEATURE:
<221> NAME/KEY: CDS
<222> LOCATION: (1)..(1179)
<223> OTHER INFORMATION:

<400> SEQUENCE: 1

```
atg gtg gtg ccg gct gct gct gcg ccg gaa tgc ggc cgc cgg gag gcg      48
Met Val Val Pro Ala Ala Ala Ala Pro Glu Cys Gly Arg Arg Glu Ala
1               5                   10                  15 gcg gcg gca gct gcg gcc gcc gtg ttc tgt cgg cgc ggc cgg ggc gtc      96
Ala Ala Ala Ala Ala Ala Ala Val Phe Cys Arg Arg Gly Arg Gly Val
            20                  25                  30 gtc gtc ccg acg gtc gac atg tcg gcg ccg gcg ggg cgc ggc gag ctg     144
Val Val Pro Thr Val Asp Met Ser Ala Pro Ala Gly Arg Gly Glu Leu
        35                  40                  45 tcg cgg cag gtg gcg cgg gcg tgc gcc ggg agc ggc ttc ttc agg gcc     192
Ser Arg Gln Val Ala Arg Ala Cys Ala Gly Ser Gly Phe Phe Arg Ala
    50                  55                  60 gtc aac cac ggc gtg ccg ccg cgg gtg tcc gcg gcg atg gac gcc ggc     240
Val Asn His Gly Val Pro Pro Arg Val Ser Ala Ala Met Asp Ala Gly
65                  70                  75                  80 gcg gcg gcg ttc ttc gcg agg gcg ggg gcc gag aag cag ctc gcc ggg     288
Ala Ala Ala Phe Phe Ala Arg Ala Gly Ala Glu Lys Gln Leu Ala Gly
                85                  90                  95 ccg ccc gac ccg ctg ggc tac ggc agc cgg agc atc ggg gcg aac ggc     336
Pro Pro Asp Pro Leu Gly Tyr Gly Ser Arg Ser Ile Gly Ala Asn Gly
            100                 105                 110 gac gtc ggc gag ctg gag tac ctg atc ctg cac gcg agc ccc gac gcg     384
Asp Val Gly Glu Leu Glu Tyr Leu Ile Leu His Ala Ser Pro Asp Ala
        115                 120                 125 gtg gcg cgc aag gcc agc gcc atc gac agg gaa gac cct cga cgg ttc     432
Val Ala Arg Lys Ala Ser Ala Ile Asp Arg Glu Asp Pro Arg Arg Phe
    130                 135                 140 agg tac gct ata gct ata cat gca gca tat gcg cga aat ttt aat cga     480
Arg Tyr Ala Ile Ala Ile His Ala Ala Tyr Ala Arg Asn Phe Asn Arg
145                 150                 155                 160 tca cga atc aca ttg cgc tcc cag gtg gta aat gat tat gtg gag gca     528
Ser Arg Ile Thr Leu Arg Ser Gln Val Val Asn Asp Tyr Val Glu Ala
                165                 170                 175 gtg agg cag ctt gct tgc cat gtc ctt gac ctg cta gga gag ggc cta     576
Val Arg Gln Leu Ala Cys His Val Leu Asp Leu Leu Gly Glu Gly Leu
```

```
                        180                 185                 190
ggc ctc agg gac ccc aca tcc ctg aca agg ctc atc aca gcc act gac    624
Gly Leu Arg Asp Pro Thr Ser Leu Thr Arg Leu Ile Thr Ala Thr Asp
        195                 200                 205 aac gac tcc ctc atc agg atc aat cac tac cct cca tcc tgc gcc gcc    672
Asn Asp Ser Leu Ile Arg Ile Asn His Tyr Pro Pro Ser Cys Ala Ala
    210                 215                 220 gcc gcc ggc gac cac aag tcc ggc ggc ggc ccg gcg ccg acg gcg gcc    720
Ala Ala Gly Asp His Lys Ser Gly Gly Gly Pro Ala Pro Thr Ala Ala
225                 230                 235                 240 atc ggg ttc ggc gag cac acc gac cct cag atc ctc agc gtc ctg cgt    768
Ile Gly Phe Gly Glu His Thr Asp Pro Gln Ile Leu Ser Val Leu Arg
                245                 250                 255 gcc aac gac gcc gac ggc ctg cag ctg ctt ctg ccg gac gcc gcc gcc    816
Ala Asn Asp Ala Asp Gly Leu Gln Leu Leu Leu Pro Asp Ala Ala Ala
            260                 265                 270 gcc ggc gac agc gtc tgg gtc ccc gtg ccg ccc gac ccg tcc gcg ttc    864
Ala Gly Asp Ser Val Trp Val Pro Val Pro Pro Asp Pro Ser Ala Phe
        275                 280                 285 ttc gtc aac gtc ggt gat ctc ctt cag gct ttg aca aac ggg agg ctg    912
Phe Val Asn Val Gly Asp Leu Leu Gln Ala Leu Thr Asn Gly Arg Leu
    290                 295                 300 gtg agt atc cgg cac agg gtg gtg gtc ggc acc ggc aag ccg agg ctg    960
Val Ser Ile Arg His Arg Val Val Val Gly Thr Gly Lys Pro Arg Leu
305                 310                 315                 320 tcg acc atc tac ttc gcg gcg ccg ccg ctg cac gcc agg atc tcg gct    1008
Ser Thr Ile Tyr Phe Ala Ala Pro Pro Leu His Ala Arg Ile Ser Ala
                325                 330                 335 ctc ccg gag acg gtg gcc gcc ggc gcg ccg cgc cgg tac agg gcc ttc    1056
Leu Pro Glu Thr Val Ala Ala Gly Ala Pro Arg Arg Tyr Arg Ala Phe
            340                 345                 350 acc tgg gcg gag tac aag agg acc atg tac acg ctc cgc ctc agc cac    1104
Thr Trp Ala Glu Tyr Lys Arg Thr Met Tyr Thr Leu Arg Leu Ser His
        355                 360                 365 aac cgc ctc gac ctc ttc cac gcc ggc gac ggc gac ggc gat gcc ggc    1152
Asn Arg Leu Asp Leu Phe His Ala Gly Asp Gly Asp Gly Asp Ala Gly
    370                 375                 380 gtt ggg gac gat gac gac cat gaa tag                                1179
Val Gly Asp Asp Asp Asp His Glu
385                 390

<210> SEQ ID NO 2
<211> LENGTH: 392
<212> TYPE: PRT
<213> ORGANISM: Oryza sativa

<400> SEQUENCE: 2

Met Val Val Pro Ala Ala Ala Pro Glu Cys Gly Arg Arg Glu Ala
1               5                   10                  15

Ala Ala Ala Ala Ala Ala Val Phe Cys Arg Arg Gly Arg Gly Val
            20                  25                  30

Val Val Pro Thr Val Asp Met Ser Ala Pro Ala Gly Arg Gly Glu Leu
        35                  40                  45

Ser Arg Gln Val Ala Arg Ala Cys Ala Gly Ser Gly Phe Phe Arg Ala
    50                  55                  60

Val Asn His Gly Val Pro Pro Arg Val Ser Ala Ala Met Asp Ala Gly
65                  70                  75                  80

Ala Ala Ala Phe Phe Ala Arg Ala Gly Ala Glu Lys Gln Leu Ala Gly
                85                  90                  95
```

```
Pro Pro Asp Pro Leu Gly Tyr Gly Ser Arg Ser Ile Gly Ala Asn Gly
            100                 105                 110

Asp Val Gly Glu Leu Glu Tyr Leu Ile Leu His Ala Ser Pro Asp Ala
        115                 120                 125

Val Ala Arg Lys Ala Ser Ala Ile Asp Arg Glu Asp Pro Arg Arg Phe
    130                 135                 140

Arg Tyr Ala Ile Ala Ile His Ala Ala Tyr Ala Arg Asn Phe Asn Arg
145                 150                 155                 160

Ser Arg Ile Thr Leu Arg Ser Gln Val Val Asn Asp Tyr Val Glu Ala
                165                 170                 175

Val Arg Gln Leu Ala Cys His Val Leu Asp Leu Leu Gly Glu Gly Leu
            180                 185                 190

Gly Leu Arg Asp Pro Thr Ser Leu Thr Arg Leu Ile Thr Ala Thr Asp
        195                 200                 205

Asn Asp Ser Leu Ile Arg Ile Asn His Tyr Pro Pro Ser Cys Ala Ala
    210                 215                 220

Ala Ala Gly Asp His Lys Ser Gly Gly Pro Ala Pro Thr Ala Ala
225                 230                 235                 240

Ile Gly Phe Gly Glu His Thr Asp Pro Gln Ile Leu Ser Val Leu Arg
                245                 250                 255

Ala Asn Asp Ala Asp Gly Leu Gln Leu Leu Pro Asp Ala Ala Ala
            260                 265                 270

Ala Gly Asp Ser Val Trp Val Pro Val Pro Pro Asp Pro Ser Ala Phe
        275                 280                 285

Phe Val Asn Val Gly Asp Leu Leu Gln Ala Leu Thr Asn Gly Arg Leu
    290                 295                 300

Val Ser Ile Arg His Arg Val Val Val Gly Thr Gly Lys Pro Arg Leu
305                 310                 315                 320

Ser Thr Ile Tyr Phe Ala Ala Pro Pro Leu His Ala Arg Ile Ser Ala
                325                 330                 335

Leu Pro Glu Thr Val Ala Ala Gly Ala Pro Arg Arg Tyr Arg Ala Phe
            340                 345                 350

Thr Trp Ala Glu Tyr Lys Arg Thr Met Tyr Thr Leu Arg Leu Ser His
        355                 360                 365

Asn Arg Leu Asp Leu Phe His Ala Gly Asp Gly Asp Gly Asp Ala Gly
370                 375                 380

Val Gly Asp Asp Asp His Glu
385                 390

<210> SEQ ID NO 3
<211> LENGTH: 984
<212> TYPE: DNA
<213> ORGANISM: Oryza sativa
<220> FEATURE:
<221> NAME/KEY: CDS
<222> LOCATION: (1)..(984)
<223> OTHER INFORMATION:

<400> SEQUENCE: 3 atg gtg gtt ctc gct ggc ccg ccc gcc gtc gat cac atc ccg ctg ctg    48
Met Val Val Leu Ala Gly Pro Pro Ala Val Asp His Ile Pro Leu Leu
1               5                   10                  15 agg tcg ccg gac ccc ggc gac gtc ttc tcc ggc gtg ccg gtc gtc gac    96
Arg Ser Pro Asp Pro Gly Asp Val Phe Ser Gly Val Pro Val Val Asp
                20                  25                  30 ctc ggc agc ccc ggc gcg gcg agg gcc gtg gtg gac gcc tgc gag cgg   144
```

```
                                                                                      -continued Leu Gly Ser Pro Gly Ala Ala Arg Ala Val Val Asp Ala Cys Glu Arg
            35                  40                  45 tac ggg ttc ttc aag gtc gtc aac cac ggc gtg gcc acg gac acg atg         192
Tyr Gly Phe Phe Lys Val Val Asn His Gly Val Ala Thr Asp Thr Met
 50                  55                  60 gac aag gcc gag tcg gag gcc gtc agg ttc ttc tcc cag acg cag ccc         240
Asp Lys Ala Glu Ser Glu Ala Val Arg Phe Phe Ser Gln Thr Gln Pro
 65                  70                  75                  80 gac aag gac cgc tcc ggc ccg gcc tac ccg ttc ggg tac ggc agc aag         288
Asp Lys Asp Arg Ser Gly Pro Ala Tyr Pro Phe Gly Tyr Gly Ser Lys
                 85                  90                  95 cgg atc ggg ttc aat ggc gac atg ggg tgg ctc gag tac ctc ctc ctc         336
Arg Ile Gly Phe Asn Gly Asp Met Gly Trp Leu Glu Tyr Leu Leu Leu
            100                 105                 110 gcc ctc gac gac gcg tcg ctc gcc gac gcc tgc acc gtc ccg tcc tgc         384
Ala Leu Asp Asp Ala Ser Leu Ala Asp Ala Cys Thr Val Pro Ser Cys
            115                 120                 125 gcg gtc ttc cgg gcc gct ctg aac gag tac atc tcg ggg gtg cgg aag         432
Ala Val Phe Arg Ala Ala Leu Asn Glu Tyr Ile Ser Gly Val Arg Lys
130                 135                 140 gtg gcg gtg cgg gtg atg gag gcg atg tcg gag ggg ctg ggc att gcg         480
Val Ala Val Arg Val Met Glu Ala Met Ser Glu Gly Leu Gly Ile Ala
145                 150                 155                 160 cag gcg gac gcg ctg agc gcg ctg gtg acg gcg gaa ggg agc gac cag         528
Gln Ala Asp Ala Leu Ser Ala Leu Val Thr Ala Glu Gly Ser Asp Gln
                165                 170                 175 gtg ttc cgc gtg aac cac tac ccg ccg tgc cgc gcg ctg cag ggg ctc         576
Val Phe Arg Val Asn His Tyr Pro Pro Cys Arg Ala Leu Gln Gly Leu
            180                 185                 190 ggc tgc agc gtc acc ggc ttc ggc gag cac acc gac ccg cag ctc gtc         624
Gly Cys Ser Val Thr Gly Phe Gly Glu His Thr Asp Pro Gln Leu Val
            195                 200                 205 tcc gtg ctc cgc tca aac ggc acg tcc ggc ctg cag atc gcg ctc cgc         672
Ser Val Leu Arg Ser Asn Gly Thr Ser Gly Leu Gln Ile Ala Leu Arg
210                 215                 220 gac ggc cag tgg gtg tcc gtg ccc tcc gac cgc gac tcc ttc ttc gtc         720
Asp Gly Gln Trp Val Ser Val Pro Ser Asp Arg Asp Ser Phe Phe Val
225                 230                 235                 240 aac gtc ggc gac tcg ttg cag gtt ctg acc aat ggg agg ttc aag agc         768
Asn Val Gly Asp Ser Leu Gln Val Leu Thr Asn Gly Arg Phe Lys Ser
                245                 250                 255 gtg aag cac agg gtg gtg gcc aac agc cta aag tct agg gtt tcc ttc         816
Val Lys His Arg Val Val Ala Asn Ser Leu Lys Ser Arg Val Ser Phe
            260                 265                 270 atc tac ttt gga ggg cca ccg tta gca cag agg att gca cca ttg cca         864
Ile Tyr Phe Gly Gly Pro Pro Leu Ala Gln Arg Ile Ala Pro Leu Pro
            275                 280                 285 cag ctg ctg ggg gag gga gag cag agc ctg tac aag gag ttc aca tgg         912
Gln Leu Leu Gly Glu Gly Glu Gln Ser Leu Tyr Lys Glu Phe Thr Trp
            290                 295                 300 gat gag tac aag aag gct gcc tac aaa tca agg ctt gga gac aac agg         960
Asp Glu Tyr Lys Lys Ala Ala Tyr Lys Ser Arg Leu Gly Asp Asn Arg
305                 310                 315                 320 ctg gcc cag ttt gag aag aag tag                                         984
Leu Ala Gln Phe Glu Lys Lys
                325

<210> SEQ ID NO 4
<211> LENGTH: 327
<212> TYPE: PRT
```

<213> ORGANISM: Oryza sativa

<400> SEQUENCE: 4

| Met | Val | Val | Leu | Ala | Gly | Pro | Pro | Ala | Val | Asp | His | Ile | Pro | Leu | Leu |
|1|||| 5 ||||| 10 ||||| 15 ||

Arg Ser Pro Asp Pro Gly Asp Val Phe Ser Gly Val Pro Val Val Asp
            20                  25                  30

Leu Gly Ser Pro Gly Ala Ala Arg Ala Val Val Asp Ala Cys Glu Arg
         35                  40                  45

Tyr Gly Phe Phe Lys Val Val Asn His Gly Val Ala Thr Asp Thr Met
        50                  55                  60

Asp Lys Ala Glu Ser Glu Ala Val Arg Phe Phe Ser Gln Thr Gln Pro
65                  70                  75                  80

Asp Lys Asp Arg Ser Gly Pro Ala Tyr Pro Phe Gly Tyr Gly Ser Lys
                85                  90                  95

Arg Ile Gly Phe Asn Gly Asp Met Gly Trp Leu Glu Tyr Leu Leu Leu
            100                 105                 110

Ala Leu Asp Asp Ala Ser Leu Ala Asp Ala Cys Thr Val Pro Ser Cys
        115                 120                 125

Ala Val Phe Arg Ala Ala Leu Asn Glu Tyr Ile Ser Gly Val Arg Lys
    130                 135                 140

Val Ala Val Arg Val Met Glu Ala Met Ser Glu Gly Leu Gly Ile Ala
145                 150                 155                 160

Gln Ala Asp Ala Leu Ser Ala Leu Val Thr Ala Glu Gly Ser Asp Gln
                165                 170                 175

Val Phe Arg Val Asn His Tyr Pro Pro Cys Arg Ala Leu Gln Gly Leu
            180                 185                 190

Gly Cys Ser Val Thr Gly Phe Gly Glu His Thr Asp Pro Gln Leu Val
        195                 200                 205

Ser Val Leu Arg Ser Asn Gly Thr Ser Gly Leu Gln Ile Ala Leu Arg
    210                 215                 220

Asp Gly Gln Trp Val Ser Val Pro Ser Asp Arg Asp Ser Phe Phe Val
225                 230                 235                 240

Asn Val Gly Asp Ser Leu Gln Val Leu Thr Asn Gly Arg Phe Lys Ser
                245                 250                 255

Val Lys His Arg Val Val Ala Asn Ser Leu Lys Ser Arg Val Ser Phe
            260                 265                 270

Ile Tyr Phe Gly Gly Pro Pro Leu Ala Gln Arg Ile Ala Pro Leu Pro
        275                 280                 285

Gln Leu Leu Gly Glu Gly Glu Gln Ser Leu Tyr Lys Glu Phe Thr Trp
    290                 295                 300

Asp Glu Tyr Lys Lys Ala Ala Tyr Lys Ser Arg Leu Gly Asp Asn Arg
305                 310                 315                 320

Leu Ala Gln Phe Glu Lys Lys
                325

<210> SEQ ID NO 5
<211> LENGTH: 382
<212> TYPE: PRT
<213> ORGANISM: Oryza sativa

<400> SEQUENCE: 5

Met Val Val Pro Ser Ala Thr Thr Pro Ala Arg Gln Glu Thr Val Val
1               5                   10                  15

Ala Ala Ala Pro Pro Ala Ala Ala Ala Ser Gly Val Val Gly Gly Gly

```
            20                  25                  30
Gly Gly Val Thr Ile Ala Thr Val Asp Met Ser Ala Glu Arg Gly Ala
        35                  40                  45
Val Ala Arg Gln Val Ala Thr Ala Cys Ala Ala His Gly Phe Phe Arg
 50                  55                  60
Cys Val Gly His Gly Val Pro Ala Ala Pro Val Ala Ala Arg Leu
 65                  70                  75                  80
Asp Ala Ala Thr Ala Ala Phe Phe Ala Met Ala Pro Ala Glu Lys Gln
                85                  90                  95
Arg Ala Gly Pro Ala Ser Pro Leu Gly Tyr Gly Cys Arg Ser Ile Gly
            100                 105                 110
Phe Asn Gly Asp Val Gly Glu Leu Glu Tyr Leu Leu Leu His Ala Asn
            115                 120                 125
Pro Ala Val Ala His Arg Ala Arg Thr Ile Asp Ala Met Asp Pro
            130                 135                 140
Ser Arg Phe Ser Ala Ile Val Asn Glu Tyr Ile Glu Ala Met Lys Lys
145                 150                 155                 160
Leu Ala Cys Glu Ile Leu Asp Leu Leu Gly Glu Gly Leu Gly Leu Lys
                165                 170                 175
Asp Pro Arg Tyr Phe Ser Lys Leu Thr Thr Asn Ala Asp Ser Asp Cys
            180                 185                 190
Leu Leu Arg Ile Asn His Tyr Pro Pro Ser Cys Asn Ile His Lys Leu
            195                 200                 205
Asp His Asp Asp Gln Cys Asn Ile Lys Ser Leu Val Ser Thr Lys Ala
    210                 215                 220
Ser Asn Gly Gly Asn Leu Met Ala Gly Gly Arg Ile Gly Phe Gly Glu
225                 230                 235                 240
His Ser Asp Pro Gln Ile Leu Ser Leu Leu Arg Ala Asn Asp Val Glu
                245                 250                 255
Gly Leu Gln Val Phe Val Pro Asp His Glu Gly Lys Glu Met Trp Val
            260                 265                 270
Gln Val Pro Ser Asp Pro Ser Ala Ile Phe Val Asn Val Gly Asp Val
            275                 280                 285
Leu Gln Ala Leu Thr Asn Gly Arg Leu Ile Ser Ile Arg His Arg Val
    290                 295                 300
Ile Ala Thr Ala Cys Arg Pro Arg Leu Ser Thr Ile Tyr Phe Ala Ser
305                 310                 315                 320
Pro Pro Leu His Ala Arg Ile Ser Ala Leu Pro Glu Thr Ile Thr Ala
                325                 330                 335
Ser Ser Pro Arg Arg Tyr Arg Ser Phe Thr Trp Ala Glu Tyr Lys Thr
            340                 345                 350
Thr Met Tyr Ser Leu Arg Leu Ser His Ser Arg Leu Glu Leu Phe Lys
        355                 360                 365
Ile Asp Asp Asp Ser Asp Asn Ala Ser Glu Gly Lys Ala
        370                 375                 380

<210> SEQ ID NO 6
<211> LENGTH: 26
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (3)..(3)
<223> OTHER INFORMATION: "n"=inosine
```

```
<220> FEATURE:
<221> NAME/KEY: misc_feature
<222> LOCATION: (9)..(9)
<223> OTHER INFORMATION: "n"=inosine
<220> FEATURE:
<221> NAME/KEY: misc_feature
<222> LOCATION: (18)..(18)
<223> OTHER INFORMATION: "n"=inosine
<220> FEATURE:
<221> NAME/KEY: misc_feature
<222> LOCATION: (24)..(24)
<223> OTHER INFORMATION: "n"=inosine

<400> SEQUENCE: 6
ggnttyggng arcayacnga yccnca                                        26

<210> SEQ ID NO 7
<211> LENGTH: 26
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (3)..(3)
<223> OTHER INFORMATION: "n"=inosine
<220> FEATURE:
<221> NAME/KEY: misc_feature
<222> LOCATION: (6)..(6)
<223> OTHER INFORMATION: "n"=inosine
<220> FEATURE:
<221> NAME/KEY: misc_feature
<222> LOCATION: (8)..(8)
<223> OTHER INFORMATION: "n"=A, G, C or T
<220> FEATURE:
<221> NAME/KEY: misc_feature
<222> LOCATION: (12)..(12)
<223> OTHER INFORMATION: "n"=inosine
<220> FEATURE:
<221> NAME/KEY: misc_feature
<222> LOCATION: (15)..(15)
<223> OTHER INFORMATION: "n"=inosine
<220> FEATURE:
<221> NAME/KEY: misc_feature
<222> LOCATION: (21)..(21)
<223> OTHER INFORMATION: "n"=inosine

<400> SEQUENCE: 7
tgnarnvnrt cnccnacrtt nacraa                                        26
```

US 7,154,028 B2

GIBBERELLIN 2-OXIDASE GENE, FUNCTIONS AND USES THEREOF

RELATED APPLICATIONS

This application claims priority to Japanese Patent Application No. 2002-276051, filed on Sep. 20, 2002. This application is also related to U.S. patent application Ser. No. 10/168,423, filed Jun. 21, 2002. The entire contents of each of these patent applications are hereby incorporated herein by reference.

FIELD OF THE INVENTION

The present invention relates to a plant gene that is involved in gibberellin biosynthesis and to the use thereof.

BACKGROUND OF THE INVENTION

Gibberellins (GAs) form a very large family of tetracyclic diterpenoid carboxylic acids that have the basic structure called ent-gibberellane. They regulate multiple processes in the life cycle of higher plants, which are essential for normal plant growth and development (Graebe, J. E. (1987) Annu. Rev. Plant Physiol., 38, 419–465; and Hooley, R. (1994) Plant Mol. Biol., 26, 1529–1555). Biologically active GAs, such as $GA_1$, are produced from trans-geranylgeranyl diphosphate mediated by sequential reactions of cyclases in the plastids, membrane-associated monooxygenases at the endoplasmic reticulum, and soluble 2-oxoglutarate-dependent dioxygenases located within the cytoplasm (Hedden, P. and Kamiya, Y. (1997) Annu. Rev. Plant Physiol. Plant Mol. Biol., 48, 431–460; and Lange, T. (1998) Planta, 204, 409–419). The biosynthetic pathway of GA is well established.

Growth of rice plants (*Oryza Sativa* L.) is regulated by the endogenous level of biologically active gibberellin, $GA_1$ (Kobayashi, M. et al., (1989) Plant Cell Physiol. 30(7): 963–969). It has been proposed that GA2-oxidase catalyzes the catabolism of biologically active GAs and their precursors in higher plants (Ross, J. J. et al., (1995) Plant J. 7: 513–523). GA2-oxidase genes have been cloned from thale cress (*Arabidopsis thaliana*), pea (*Pisum sativum*) and bean (*Phaseolus coccineus*) (Lester, D. R. et al., (1999) Plant J., 19:65–73; Martin, D. N. et al., (1999) Plant Physiol., 121: 775–781; and Thomas S. G. et al., (1999) Proc. Natl. Acad. Sci. USA 96:4698–4703). Thomas et al. (supra) reported that the transcription levels of *Arabidopsis* GA2-oxidase genes, AtGA2ox1 and AtGA2ox2, were reduced in GA-deficient mutants, but the levels increased after treatment with $GA_3$. Based on these results, these researchers concluded that GA2-oxidase is associated with the maintenance of the concentration of biologically active GAs in plant tissues.

The present inventors also reported the cloning and characterization of the rice GA2-oxidase gene, OsGA2ox1 (Sakamoto, T. et al. (2001) Plant Physiol. 125(3): 1508–16). The OsGA2ox1 gene product catalyzed the metabolism of $GA_{20}$ into $GA_{29}$, and $GA_1$ into $GA_8$. However, the transcription level of OsGA2ox1 was not affected by $GA_3$-treatment.

SUMMARY OF THE INVENTION

An objective of the present invention is to determine the DNA sequence of a GA2-oxidase gene that regulates the height of rice plants, and to provide a technique for regulating their height via this DNA (by controlling the endogenous gibberellin content). Another objective of the present invention is to modify the height of plants other than rice.

The present inventors employed PCR using degenerate primers in order to isolate a novel gene for rice GA2-oxidase. As a result, three DNA fragments were obtained. One of these fragments had a sequence that matched the previously identified sequence of OsGA2ox1. The other two fragments were novel genes (designated OsGA2ox2 and OsGA2ox3).

Expression patterns of OsGA2ox2 and OsGA2ox3 in various rice tissues were investigated by the present inventors via RNA gel blot analysis and gel blotting of RT-PCR products. OsGA2ox3 expression was observed in all the tissues examined. It was shown that OsGA2ox3 expression is regulated by the concentration of biologically active GAs in a feedforward manner. The OsGA2ox3 gene product is the first enzyme found in monocotyledons that can mediate the two-step oxidation of $GA_{20}$ to $GA_{29}$ and $GA_{29}$ to $GA_{29}$-catabolites. It was also shown that the growth of transgenic rice plants, that express OsGA2ox3, was suppressed as compared to control plants.

The present invention relates to DNAs with gibberellin 2-oxidation activity and use thereof. Specifically, the invention provides the following:

(1) a DNA encoding a plant protein having gibberellin 2 oxidation activity, wherein said DNA is selected from the group consisting of:
  (a) a DNA encoding a protein comprising the amino acid sequence as set forth in SEQ ID NO: 2 or 4;
  (b) a DNA comprising a coding region of the nucleotide sequence as set forth in SEQ ID NO: 1 or 3;
  (c) a DNA encoding a protein comprising the amino acid sequence as set forth in SEQ ID NO: 2 or 4, wherein one or more amino acid residues are substituted, deleted, added, and/or inserted; and
  (d) a DNA hybridizing to the DNA comprising the nucleotide sequence as set forth in SEQ ID NO: 1 or 3 under stringent conditions;

(2) the DNA according to (1), wherein said DNA catalyzes the conversion of gibberellin $A_{20}$ to gibberellin $A_{29}$, which is further metabolized to gibberellin $A_{29}$-catabolite;

(3) the DNA according to (1) or (2), wherein said plant is a monocotyledon;

(4) a DNA selected from the group consisting of:
  (a) a DNA encoding an antisense RNA complementary to the transcript of the DNA according to any one of (1) to (3);
  (b) a DNA encoding an RNA having the ribozyme activity that specifically cleaves the transcript of a DNA according to any one of (1) to (3);
  (c) a DNA encoding an RNA that suppresses the expression of a DNA according to any one of (1) to (3) in plant cells via RNAi; and
  (d) a DNA encoding an RNA that suppresses the expression of a DNA according to any one of (1) to (3) in plant cells by co-suppression;

(5) a protein encoded by a DNA according to any one of (1) to (3);

(6) a vector harboring a DNA according to any one of (1) to (4);

(7) a transformed plant cell harboring a DNA according to any one of (1) to (4), or harboring the vector according to (6);

(8) a transgenic plant comprising the transformed plant cell according to (7);

(9) a transgenic plant that is an offspring or clone of the transgenic plant according to (8), wherein plant cells from said offspring also contains the DNA of any one of (1) to (4);

(10) a propagation material obtained from the transgenic plant according to (8) or (9);

(11) a method of producing the transgenic plant according to (8), which comprises the steps of introducing a DNA according to any one of (1) to (4) or the vector according to (6) into a plant cell and regenerating a plant from said plant cell;

(12) a plant growth suppressor comprising a DNA according to any one of (1) to (3) as an active ingredient;

(13) a plant growth suppressor, comprising the DNA according to (4) as an active ingredient;

(14) a method of suppressing plant growth, which comprises expressing a DNA according to any one of (1) to (3) in plant cells;

(15) a method of promoting plant growth, which comprises suppressing the endogenous expression of a DNA according to any one of (1) to (3) in plant cells; and

(16) the method according to (15), which comprises introducing the DNA according to (4) into plant cells.

BRIEF DESCRIPTION OF THE DRAWINGS

FIG. 1 shows the characteristic features of the sequences of rice GA2-oxidases. Deduced amino acid sequences of rice GA2-oxidases are aligned. Sequences conserved among the three enzymes are indicated in grey. Triangles indicate the amino acid residues involved in the proposed active center of 2-oxoglutarate-dependent dioxygenases.

DETAILED DESCRIPTION OF THE INVENTION

Figure 2:
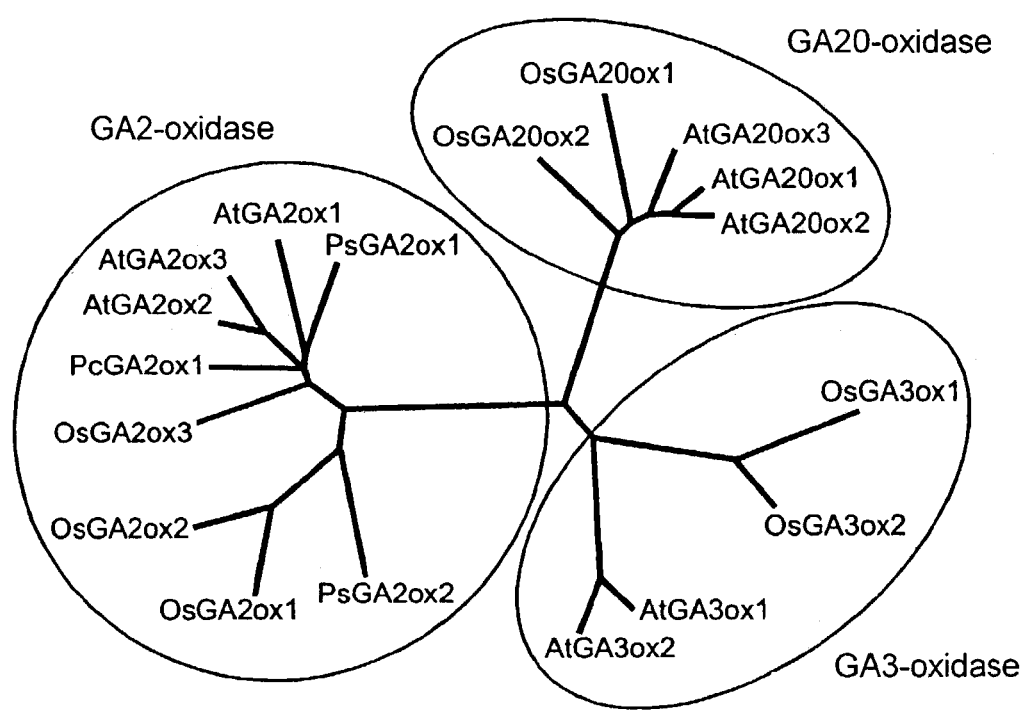
FIG. 2 shows the phylogenetic tree of GA20-, GA3- and GA2-oxidases inferred from the amino acid sequences.
GA20-oxidases derived from thale cress (*Arabidopsis thaliana*):
AtGA20ox1 (X83379)
AtGA20ox2 (X83380), and
AtGA20ox3 (X83381);
GA20-oxidases derived from rice (*Oryza sativa*):
OsGA20ox1 (U50333), and
OsGA20ox2 (AB077025),);
GA3-oxidases derived from thale cress (*Arabidopsis thaliana*):
AtGA3ox1 (L37126), and
AtGA3ox2 (AF070937);
GA3-oxidases derived from rice (*Oryza sativa*):
OsGA3ox1 (AB054084), and
OsGA3ox2 (AB056519);
GA2-oxidases derived from thale cress (*Arabidopsis thaliana*):
AtGA2ox1 (AJ132435),
AtGA2ox2 (AJ132436), and
AtGA2ox3 (AJ132437);
GA2-oxidase derived from bean (*Phaseolus coccineus*):
PcGA2ox1 (At132438);
GA2-oxidase derived from pea (*Pisum sativum*):
PsGA2ox1 (AF100954), and
PsGA2ox2 (AF100955);
GA2-oxidase derived from rice (*Oryza sativa*):
OsGA2ox1 (AB059416),
OsGA2ox2, and
OsGA2ox3.

The present invention provides DNAs encoding plant-derived proteins that have gibberellin (GA) 2-oxidation activity.

GA2-oxidases irreversibly inactivate active GAs and their precursors. Thus, the DNAs encoding proteins having gibberellin (GA) 2-oxidation activity of the present invention may be utilized to produce biologically inactive GAs.

Furthermore, studies on GA-deficient mutants and the effect of exogenous GAs and/or GA synthesis inhibitors on plants have revealed that GAs are essential, strong regulators of plant growth. These GAs influence various phenomena in the growth of plants having a relatively high stature, and are also involved in the stimulation of stem elongation. Therefore, DNAs of the present invention may be useful in modifying plant growth, for example, to produce plants that are different to the wild types. Modification of plants, dwarfing in particular, provides a variety of agronomical advantages such as a high planting density, efficient photo-reception, decrease in wind damage, reduction of farming labor, etc. Dwarfing is thus the most valuable trait for breeding agricultural and horticultural products, including fruit trees.

As used herein, the phrase "GA2 oxidation activity" refers to the activity that catalyzes the metabolism from the substrates, $C_{19}$-GAs, to corresponding 2β-hydroxides (e.g. from $GA_1$, $GA_4$, $GA_9$ and $GA_{20}$ to $GA_8$, $GA_{34}$, $GA_{51}$ and $GA_{29}$, respectively). Preferably, this activity suppresses the metabolism to $GA_1$, an active gibberellin present in the stems and leaves of various higher plants, by catalyzing the metabolism of $GA_{20}$, which is a direct precursor of $GA_1$, to inactive $GA_{29}$ and $GA_{29}$-catabolites. In general, such an activity may be detected by the following steps: a DNA encoding a protein having a GA2-oxidation activity of the present invention is inserted into an expression vector; the protein is overexpressed as a fusion protein in *E. coli* cells; the resulting cell extract is used as an enzyme solution to carry out the in vitro reaction in the presence of substrates $C_{19}$-GAs or $GA_{29}$, and cofactors such as iron ions and 2-oxoglutarate; and finally, the reaction product is verified using gas chromatography-mass spectrometry method (GC-MS).

In the present invention, plants from which a DNA encoding a protein having GA2-oxidation activity is obtained, include, but are not limited to, rice, oats such as wheat and barley, corn, *Arabidopsis thaliana*, *Pisum sativum*, and *Phaseolus coccineus*.

Plants whose growth can be modified by introducing a DNA of the present invention include, but are not limited to, crops and ornamental plants. Specifically, crops include monocotyledon s such as rice, and dicotyledons such as soybean and potato. Ornamental plants include flower plants such as chrysanthemum, morning glory, poinsettia, and cosmos. Fruit trees include apple, orange, and pear.

In the present invention, DNAs encoding plant proteins having GA2-oxidation activity include, for example, a DNA comprising the coding region of the nucleotide sequence of SEQ ID NO: 1 or 3 (the respective cDNA sequences of OsGA2ox2 and OsGA2ox3), and the DNA encoding the protein comprising the amino acid sequence of SEQ ID NOs: 2 or 4 (the respective amino acid sequences of OsGA2ox2 and OsGA2ox3). The proteins encoded by OsGA2ox2 and OsGA2ox3, which were isolated by the present inventors, retained an amino acid residue bound to Fe at the active site, and showed a significant sequence homology to other GA2-oxidases. Thus, the OsGA2ox2 and OsGA2ox3 cDNAs, which were isolated by the present inventors, are considered to encode GA2-oxidases.

The present invention is also directed to a DNA encoding a protein having a GA2-oxidation activity, which DNA is structurally similar to a protein comprising the amino acid sequence of SEQ ID NO: 2 or 4.

Whether or not a certain DNA encodes a protein having a GA2-oxidation activity can be determined by examining, for example, whether the protein encoded by the DNA catalyzes the metabolism from $C_{19}$-GAs to the corresponding 2β-hydroxides, or whether the protein catalyzes the metabolism from $GA_{29}$ to $GA_{29}$-catabolites. It may also be determined by observing whether the growth of plants into which the DNA has been introduced (by methods similar to those described in Examples) is suppressed or not.

Examples of such DNAs include those encoding mutants, derivatives, alleles, variants, and homologues comprising the amino acid sequence of SEQ ID NO: 2 or 4, wherein one or more amino acids are substituted, deleted, added and/or inserted.

Examples of well known methods for preparing a DNA encoding a protein comprising altered amino acids include site-directed mutagenesis (Kramer, W. and Fritz, H. -J. Methods in Enzymology, 154: 350–367 (1987)). The amino acid sequence of a protein may also be spontaneously mutated due to a mutation of its corresponding nucleotide sequence. A DNA encoding a protein having the amino acid sequence of a protein with a GA2-oxidation activity where one or more amino acids are substituted, deleted, added, and/or inserted are also included within the scope of DNAs encoding proteins with GA2-oxidation activity of the present invention, provided they encode a protein functionally equivalent to the natural protein with a GA2-oxidation activity (SEQ ID NO: 2 or 4). Additionally, nucleotide sequence mutants that do not give rise to amino acid sequence changes in the protein (degenerate mutants) are also included within the scope of DNAs of with GA2-oxidation activity of the present invention.

The number of amino acids that are mutated is not particularly restricted, as long as a GA2-oxidation activity is maintained. Normally, it is within 50 amino acids, preferably within 30 amino acids, more preferably within 10 amino acids, and even more preferably within 3 amino acids. The site of mutation may be any site, as long as the GA2-oxidation activity is maintained.

An amino acid substitution is preferably a mutation into a different amino acid(s) in which the properties of the amino acid side-chain are conserved. The substitution may be a conservative amino acid substitution. A "conservative amino acid substitution," as employed in the present invention, refers to a replacement of one amino acid residue belonging to one of the following groups with similar side chain(s) with another amino acid from the same group. Groups of amino acid residues having similar side chains are well known to one of ordinary skill in the art. These groups include the following: amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); beta-branched side chains (e.g., threonine, valine, isoleucine); and aromatic side chains (e.g., tyrosine, phenylalanine, tryptophan, histidine).

DNAs encoding proteins functionally equivalent to proteins with GA2-oxidation activity described in SEQ ID NO: 2 or 4 can be produced, for example, via methods well known to those skilled in the art. These methods include: methods using hybridization techniques (Southern, E. M. Journal of Molecular Biology, 98: 503, (1975)); and polymerase chain reaction (PCR) techniques (Saiki, R. K. et al. Science, 230: 1350–1354, (1985); Saiki, R. K. et al. Science, 239: 487–491, (1988)). It is routine for a person skilled in the art to isolate a DNA with a high homology to a protein with a GA2-oxidation activity from rice and other plants using as a probe, the nucleotide sequence of OsGA2ox2 or OsGA2ox3 cDNA (SEQ ID NO: 1 or 3), or a part thereof, and an oligonucleotide hybridizing specifically to the nucleotide sequence of OsGA2ox2 or OsGA2ox3 cDNA as a primer. Such DNAs encoding proteins functionally equivalent to proteins with GA2-oxidation activity, obtainable by hybridization or PCR techniques, are included within the scope of the DNAs of this invention.

Hybridization reactions to isolate such DNAs are preferably conducted under stringent conditions. The phrase "stringent hybridization conditions" according to the present invention includes conditions such as the following: 6 M urea, 0.4% SDS, and 0.5×SSC. DNAs with higher homology are expected when hybridization is performed under hybridization conditions with greater stringency such as the following: 6 M urea, 0.4% SDS, and 0.1×SSC. As used herein, the phrase "high homology" through the entire amino acid sequence means an identity of at least 50% or more, preferably 70% or more, and more preferably 90% or more, and most preferably 95% or more.

The degree of amino acid sequence identity or nucleotide sequence identity can be determined by using the BLAST algorithm developed by Karlin and Altschul (Karlin and Altschul. Proc. Natl. Acad. Sci. USA, 87: 2264–2268, (1990); and Karlin and Altschul. Proc. Natl. Acad. Sci. USA, 90: 5873–5877, (1993)). Programs referred to as BLASTN and BLASTX, which are based on the BLAST algorithm, have been developed (Altschul, S. F. et al. J. Mol. Biol. 215: 403, (1990)). To analyze nucleotide sequences by BLASTN, the parameters are set at, for example, score=100 and word length=12. On the other hand, the parameters used for the analysis of amino acid sequences by BLASTX are set at, for example, score=50 and word length=3. Specific techniques for such analyses are known in the art (Please see the website of the National Center for Biotechnology Information, USA; http://www.ncbi.nlm.nih.gov)

DNAs of the present invention include genomic DNAs, cDNAs, and chemically synthesized DNAs. A genomic DNA or cDNA can be prepared according to conventional methods known to those skilled in the art. More specifically, genomic DNA can be prepared as follows: (1) extract a genomic DNA from rice cultivars having a DNA encoding a protein with a GA2-oxidation activity; (2) construct a genomic library (utilizing a vector such as a plasmid, phage, cosmid, BAC, or PAC); (3) spread the library; and (4) conduct colony hybridization or plaque hybridization using a probe prepared based on a DNA encoding a protein with a GA2-oxidation activity of the present invention (e.g., SEQ ID NO: 1 or 3). Alternatively, a genomic DNA can be prepared via PCR using primers specific for a DNA encoding a protein with a GA2-oxidation activity of the present invention (e.g., SEQ ID NO: 1 or 3). cDNA can be prepared as follows: (1) synthesize cDNAs based on mRNAs extracted from rice cultivars (e.g., Nipponbare) having a DNA encoding a protein with a GA2-oxidation activity; (2) prepare a cDNA library by inserting the synthesized cDNA into a vector such as λZAP; (3) spread the cDNA library; and (4) conduct colony hybridization or plaque hybridization as described above. Alternatively, cDNA can also be prepared by PCR.

Furthermore, the present invention provides proteins with a GA2-oxidation activity. These proteins can be produced as recombinant or naturally-occurring proteins by a method known to one skilled in the art. Recombinant proteins can be produced, as described below. First, a DNA encoding a protein with a GA2-oxidation activity of the present invention is synthesized by RT-PCR using primers having restriction enzyme sites and subcloned into multi-cloning sites of the pMAL-c2 expression vector (NEB). This construct is used to transform *Escherichia coli* strain BL21 cells (protease-deficient strain) by standard methods. Using the transformant thus obtained, the protein is induced. *Escherichia coli* are cultured (by shaking) in a 2×YT medium containing 0.2% glucose at 37° C. When the $OD_{600}$ value reaches around 0.6, IPTG is added to a final concentration of 1 mM, and cultured further at 18° C. for 24 h. Extraction of an enzyme solution is performed as follows. After culturing, cells are collected and suspended in a suspension buffer (50 mM Tris-HCl (pH 8.0) containing 10% glycerol, 2 mM DTT, and 1 mg/ml lysozyme). The cell suspension is allowed to stand at 4° C. for 30 minutes, and then incubated at −80° C. until it becomes completely frozen. The frozen suspension is thawed and sonicated for 30 seconds twice at 5-minute intervals at the MAX level using a Sonicator (Heat Systems-Ultrasonics, Inc., Model W-225R). The suspension thus treated is centrifuged (at 15,000 rpm and 4° C. for 20 minutes), and the supernatant is used as a crude enzyme solution.

Furthermore, the purified protein can be prepared by expressing a protein with a GA2-oxidation activity of this invention in *E. coli* or such as a fusion protein with a histidine tag, maltose-binding protein, or glutathione-S-transferase (GST), and subsequently purifying them on a nickel column, an amylose-column, or a GST-glutathione column, respectively. Then, after the purification, the above-described tag can be cleaved off using restriction proteases, such as, thrombin and factor Xa as required. When naturally-occurring proteins are used, such a protein can be purified for example by the following steps of: preparing a recombinant protein or partial peptide of the protein; immunizing a suitable animal with the protein to prepare an antibody; binding the antibody to an affinity column; and contacting with the column an extract from plants such as rice expressing the present protein.

A DNA encoding a protein of the present invention that has GA2-oxidation activity may be used to suppress plant growth (e.g., for dwarfing) as a growth suppressor. To produce a transgenic plant showing growth suppression, the DNA is inserted into an appropriate vector, and then, the vector is introduced into plant cells according to the method described below, followed by regeneration of the resulting transgenic plant cells. The present invention provides such methods for suppressing plant growth.

The present invention also provides a method for promoting plant growth. A transgenic plant showing accelerated growth may be produced, for example, by inserting a DNA that suppresses the expression of a DNA encoding a protein having a GA2-oxidation activity into an appropriate vector, then introducing the vector into plant cells according to the method described below, followed by regenerating the resulting transgenic plant cells. Thus, a DNA that suppresses the expression of a DNA encoding a protein having GA2-oxidation activity can be used as a plant growth enhancer.

The phrase "suppression of the expression of a DNA encoding a protein having a GA2-oxidation activity," as employed herein, includes the suppression of the transcription of the DNA and suppression of the translation into the protein. It also includes reducing the expression as well as complete arrest of the expression. It further includes cases in which the translated protein does not show its natural effects in plant cells.

The expression of a specific endogenous gene in plants can be suppressed by conventional methods utilizing antisense technology. Ecker et al. were the first to demonstrate the effect of an antisense RNA introduced by electroporation in plant cells (Ecker, J. R. and Davis, R. W. Proc. Natl. Acad. Sci. USA 83:5372, (1986)). Thereafter, target gene expression was reportedly reduced in tobacco and petunias by expressing antisense RNAs (van der Krol, A. R. et al. Nature 333: 866, (1988).). The antisense technique has now been established as a means to suppress target gene expression in plants.

Multiple factors cause an antisense nucleic acid to suppress target gene expression. These include inhibition of transcription initiation by triple strand formation; inhibition of transcription by hybrid formation at a site where the RNA polymerase has formed a local open loop structure; transcription inhibition by hybridization with the RNA being synthesized; inhibition of splicing by hybrid formation at the junction between an intron and an exon; inhibition of splicing by hybrid formation at the site of spliceosome formation; inhibition of mRNA translocation from the nucleus to the cytoplasm by hybridization with mRNA; inhibition of splicing by hybrid formation at the capping site or at the poly A addition site; inhibition of translation initiation by hybrid formation at the binding site for the translation initiation factors; inhibition of translation by hybrid formation at the site for ribosome binding near the initiation codon; inhibition of peptide chain elongation by hybrid formation in the translated region or at the polysome binding sites of mRNA; and inhibition of gene expression by hybrid formation at the sites of interaction between nucleic acids and proteins. These antisense nucleic acids suppress the target gene expression by inhibiting many processes such as transcription, splicing, and translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society Ed.), Tokyo Kagaku Dozin, pp. 319–347, (1993)).

An antisense sequence used in the present invention can suppress target gene expression by any of the above-mentioned mechanisms. If an antisense sequence is designed to be complementary to the untranslated region near the 5' end of the gene's mRNA, it will effectively inhibit translation of a gene. Additionally, it is also possible to use sequences that are complementary to the coding regions or to the untranslated regions on the 3' side. Thus, the antisense DNA used in the present invention includes a DNA having antisense sequences against both the untranslated regions and the translated regions of the gene. The antisense DNA to be used is ligated downstream from an appropriate promoter, and, preferably, a sequence containing the transcription termination signal is ligated to the 3' side. The DNA thus prepared can be transfected into a desired plant by known methods. The sequence of the antisense DNA is preferably a sequence complementary to the endogenous gene of the plant to be transformed, or a part thereof, but it need not be perfectly complementary so long as it can effectively suppress gene expression. The transcribed RNA is preferably not less than 90%, and most preferably not less than 95% complementary to the transcribed products of the target gene. In order to effectively suppress the expression of a target gene by means of an antisense sequence, the antisense DNA should be at least 15 nucleotides long or more, preferably 100 nucleotides long or more, and even more preferably 500 nucleotides long or more. An antisense DNA to be used is generally shorter than 5 kb, and preferably shorter than 2.5 kb.

Polynucleotides encoding ribozymes can also be used to suppress the expression of endogenous genes. A ribozyme is a RNA molecule that has catalytic activity. This novel class of catalytic RNAs cleaves RNA phosphodiester bonds at specific sites within their own RNA sequence (cis cleavage) or in other RNA molecules (trans cleavage). In self-cleavage reactions, unlike enzymes, the ribozyme is not acting like a true catalyst because it gets modified during the course of the reaction. Research focusing on ribozymes as RNA-cleaving enzymes has enabled the design of a ribozyme that site-specifically cleaves RNA. While some ribozymes of the group I intron type or the M1RNA contained in RNaseP consist of 400 nucleotides or more, others belonging to the hammerhead-type or the hairpin-type have an activity domain of about 40 nucleotides (Makoto Koizumi and Eiko Ohtsuka, Tanpakushitsu Kakusan Kohso (Nucleic acid, Protein, and Enzyme), 35: 2191, (1990)). The self-cleaving domain of a hammerhead type ribozyme cleaves at the 3' side of C15 in the sequence G13U14C15. Formation of a nucleotide pair between U14 and A9 is considered important for ribozyme activity. Furthermore, it has been shown that the cleavage also occurs at the position of A15 or U15 instead of C15 (Koizumi, M. et al. (1988). FEBS Lett. 228, 228). If the substrate-binding site of the ribozyme is designed to be complementary to the RNA sequences adjacent to the target site, one can create a restriction-enzyme-like RNA-cleaving ribozyme that recognizes the sequence UC, UU, or UA within the target RNA (Koizumi, M. et al. FEBS Lett. 239: 285, (1988); Koizumi, Makoto and Ohtsuka, Eiko (1990). Tanpakushitsu Kakusan Kohso (Protein, Nucleic acid, and Enzyme), 35, 2191; Koizumi, M. et al. Nucleic Acids Res. 17: 7059, (1989).). For example, in the coding region of a DNA encoding a protein with a GA2-oxidation activity (SEQ ID NO: 1 or 3), there are several sites that can be used as ribozyme targets.

Hairpin type ribozymes are also useful in the present invention. A hairpin type ribozyme can be found, for example, in the minus strand of the satellite RNA of tobacco ringspot virus (Buzayan, J. M. (1986). Nature 323, 349). This hairpin type ribozyme has also been shown to target-specifically cleave RNA (Kikuchi, Y. and Sasaki, N. (1992). Nucleic Acids Res. 19, 6751; Kikuchi, Yo (1991) Kagaku To Seibutsu (Chemistry and Biology) 30, 112).

A ribozyme designed to cleave a target is fused with a promoter such as the cauliflower mosaic virus 35S promoter, and with a transcription termination sequence, so that it will be transcribed in plant cells. If extra sequences are added to the 5' end or the 3' end of the transcribed RNA, the ribozyme activity may be lost. In this case, one can place an additional trimming ribozyme, which functions in the cis position against the 5' or the 3' side of the ribozyme portion, thereby precisely cutting the ribozyme portion from the transcribed RNA containing the ribozyme (Taira, K. et al. (1990). Protein Eng. 3, 733; Dzaianott, A. M. and Bujarski, J. J. (1989). Proc. Natl. Acad. Sci. USA 86, 4823; Grosshands, C. A. and Cech, R. T. (1991). Nucleic Acids Res. 19, 3875; Taira, K. et al. (1991.) Nucleic Acid Res. 19, 5125). Multiple sites within a target gene can be cleaved by arranging these structural units in tandem to achieve greater effects (Yuyama, N. et al., (1992). Biochem. Biophys. Res. Commun. 186, 1271). As described above, by using ribozymes, it is possible to specifically cleave transcription products of a target gene of the present invention, thereby suppressing the expression of the gene.

Endogenous gene expression may also be suppressed by means of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (Chuang, C. F. & Meyerowitz, E. M., Proc. Natl. Acad. Sci. USA 97: 4985, 2000). For example, to achieve suppression of the expression of a DNA encoding a protein having a GA2-oxidation activity by means of RNAi, a double-stranded RNA having the sequence of a DNA encoding a protein having a GA2-oxidation activity (SEQ ID NO: 1 or 3), or an analogous sequence thereof, is introduced into plants of interest. Then, the resulting plants are screened for a phenotype showing delayed flowering compared to the wild-type plants. Although the genes used for RNAi need not be completely identical to the target gene, they are at least 70% or more identical to the target gene sequence, preferably at least 80% or more, more preferably 90% or more, and most preferably 95%. The sequence identity may be determined using a method described above.

Endogenous gene expression can also be co-suppressed through the transformation with a DNA having a sequence identical or similar to the target gene sequence. The term "co-suppression," as employed herein, refers to the phenomenon in which, when a gene having a sequence identical or similar to that of the target endogenous gene is introduced into plants by transformation, expression of both the introduced exogenous gene and the target endogenous gene is suppressed. Although the detailed mechanism of co-suppression is unknown, at least a part of the mechanism appears to overlap with RNAi (Smyth, D. R., Curr. Biol., 7: R793, (1997); and Martienssen, R., Curr. Biol., 6: 810, (1996)). For example, to obtain a plant in which a DNA encoding a protein having a GA2-oxidation activity is co-suppressed, plants of interest are transformed with a vector DNA construct that expresses the DNA encoding a protein having a GA2-oxidation activity, or a DNA having a sequence similar thereto, and screened for plants showing delayed flowering compared to the wild type plants. The gene to be used for co-suppression need not be completely identical to the target gene. However, it should have at least 70% or more, preferably 80% or more, more preferably 90% or more, and most preferably 95% or more sequence identity. The sequence identity may be determined using a method described above.

The present invention provides methods for producing a transgenic plant, comprising the steps of introducing the DNA of the present invention into plant cells and regenerating a plant from the plant cells.

In the present invention, plants, from which plant cell is derived, are not particularly restricted. In addition, vectors used for the transformation of plant cells are not limited to any particular type as long as the vector can express the inserted genes in plant cells. For example, vectors comprising promoters for constitutive gene expression in plant cells (e.g., cauliflower mosaic virus 35S promoter); and promoters inducible by exogenous stimuli can be used. The term "plant cell" used herein includes various forms of plant cells, such as cultured cell suspensions, protoplasts, leaf sections, and calluses.

A vector can be introduced into plant cells by known methods such as the polyethylene glycol method, electroporation, *Agrobacterium*-mediated transfer, and particle bombardment. One of methods mediated *Agrobacterium* (e.g. EHA101 strain), for example, ultra-fast transformation technique for monocotyledons (Japan Patent No. 3,141,084) can be used. In particle bombardment, a device from Bio-Rad may be used. Plants can be regenerated from transformed plant cells by known methods depending on the type of plant cell (Toki et al., Plant Physiol. 100:1503–1507 (1995)).

Some of the transformation and regeneration methods for rice plants include: (1) introducing genes into protoplasts using polyethylene glycol and regenerating the plant (suitable for indica rice cultivars) (Datta, S. K., in "Gene Transfer To Plants", Potrykus I and Spangenberg Eds., pp66–74 (1995)); (2) introducing genes into protoplasts using electric pulse, and regenerating the plant (suitable for japonica rice cultivars)(Toki et al., Plant Physiol. 100: 1503–1507 (1992)); (3) introducing genes directly into cells by particle bombardment and regenerating the plant (Christou et al., Bio/Technology, 9: 957–962 (1991)); (4) introducing genes using *Agrobacterium*, and regenerating the plant (Hiei et al., Plant J. 6: 271–282 (1994)) These methods are well established in the art and are widely used in the technical field of the present invention. These methods can be suitably used in the present invention.

Once a transformed plant having a DNA of the present invention is introduced into the genome is obtained, it is possible to obtain progenies from that plant by sexual or asexual reproduction. Alternatively, plants can be mass-produced from propagation materials (for example, seeds, fruits, ears, tubers, tubercles, tubs, calluses, protoplasts, etc.) obtained from the plant, as well as progenies or clones thereof.

The present invention provides novel DNAs involved in the inactivation of plant gibberellins as well as plants whose gibberellin activity has been modified by regulating the expression of these DNAs. This invention enables modification of gibberellin activation in plants so as to artificially modify plant types. Specifically, the present invention revealed major GA2-oxidase genes, making it easier to accelerate plant growth. Inactivation of gibberellin within plants induces dwarf plant phenotypes due to suppression of longitudinal growth. This invention could prevent rice plants from bending over when excessive growth is promoted due to ample fertilization. As a result, a substantial increase in crops could result due to enhanced efficiency of light reception to leaves. It is also possible to improve efficiency of harvesting and breeding. Another effect of the present invention is to increase the yield of the whole plant by suppressing the expression of DNAs of this invention in the plant, thereby promoting gibberellin activation therein. This later strategy is particularly beneficial in improving the yield of feed crops as a whole.

Any patents, patent applications, and publications cited herein are incorporated by reference in their entireties.

The present invention will be specifically described below with reference to Examples, but it is not to be construed as being limited thereto.

(1) Plant Material

Seeds of wild-type rice (*Oryza sativa* L., i.e. Nipponbare) were sterilized in 1% NaClO for one hour, and seeded on agar medium. Seedlings were grown in a growth chamber under continuous light at 30° C. To investigate the influence of $GA_3$ and uniconazole on GA-oxidase expression, wild-type rice seedlings were transferred to a hydroponic culture system containing 10 µM $GA_3$ or 10 µM uniconazole, and allowed to grow for three days.

(2) Molecular Cloning and Sequencing of Rice GA2-Oxidase Genes

To amplify GA2-oxidase genes from rice plants, PCR was performed using two degenerate primers (forward primer: 5'-GGITTYGGIGARCAYACIGAYCCICA-3' (SEQ ID NO: 6); and reverse primer: 5'-TGIARIVNRTCICCIACRTTIA-CRAA-3' (SEQ ID NO: 7)). They were designed based on regions conserved among GA20-oxidases (AtGA20ox1 (X83379), AtGA20ox2 (X83380), AtGA20ox3 (X83381), and OsGA20ox1 (U50333)); and GA3-oxidases (OsGA3ox1 (AB054084) and OsGA3ox2 (AB056519)). The amplified fragments were cloned into pCR II (Invitrogen, Carlsbad, Calif., USA) and then sequenced. As previously described (Sakamoto, T. et al., Plant Physiol., 125(3): 1508–16, 2001), a rice genomic library was screened using subcloned PCR fragments. The nucleotide and amino acid sequences were analyzed using the CLUSTALW program (found on the website of the DNA Data Bank of Japan (DDBJ); http://www.ddbj.nig.ac.jp/E-mail/homology.html).

(3) Expression Analysis

Ten-micrograms of RNAs were prepared from each sample, and gel blot analysis was performed as previously described (Sakamoto, T. et al., Plant Physiol., 125(3): 1508–16, 2001).

(4) Enzyme Assay

A cell lysate obtained from *E. coli* heterologously expressing OsGA2ox3 cDNA was used for enzyme assay as previously described (Sakamoto, T. et al., Plant Physiol., 125(3): 1508–16, (2001)).

(5) Construction of Plasmid and Transformation of Plant

As previously described (Sakamoto, T. et al., Plant Physiol., 125(3): 1508–16, 2001), the full-length OsGA2ox3 cDNA was inserted between the rice actin promoter and the polyadenylation signal of nopaline synthase (NOS) present in a hygromycin resistant binary vector pAct-Hm2. This construct was introduced into *Agrobacterium tumefaciens* EHA101. *Agrobacterium*-mediated transformation was conducted as described in the literature (WO 01/06844 A1). Transgenic plants were selected on a medium containing 50 mg/L hygromycin.

EXAMPLE 1

Three DNA fragments were obtained by PCR using the generate primers. One of the fragments was identical to OsGA2ox1 that has already been identified. The other two fragments encoded novel genes (designated OsGA2ox2 and OsGA2ox3). These clones were used for screening a genomic library to obtain full-length genomic clones. After sequencing the genomic clones, putative open reading frame (ORF) of OsGA2ox3 was amplified by RT-PCR. RT-PCR was unsuccessful for OsGA2ox2.

The putative OsGA2ox2 ORF comprises a 1176 bp sequence encoding a protein consisting of 392 amino acids. The OsGA2ox3 ORF amplified by RT-PCR contained a 981 bp sequence encoding a protein consisting of 327 amino acids. In the active center, the amino acid sequence in which $Fe^{2+}$ is positioned (Valegard, K. et al., Nature 394: 805–809, (1998)) was highly conserved (FIG. 1). The amino acid sequences logically deduced from the two genes were compared with those of other 2-oxoglutarate-dependent dioxygenase genes involved in gibberellin biosynthesis (FIG. 2). The GA2-oxidase gene family can be classified into two sub-families. The OsGA2ox3 and *Arabidopsis* GA2-oxidase genes are grouped into the same sub-family. All the members of this sub-family, except AtGA2ox1, catalyzed multi-step reactions. On the other hand, OsGA2ox1, OsGA2ox2, and PsGA2ox2 are the members of the other sub-family, and the OsGA2ox1 gene product catalyzed a single step oxidation. The sequences of OsGA2ox2 and OsGA2ox3 showed significant homology to the sequence of the GA2-oxidase gene, demonstrating that OsGA2ox2 and OsGA2ox3 encode GA2-oxidase.

EXAMPLE 2

Figure 3:
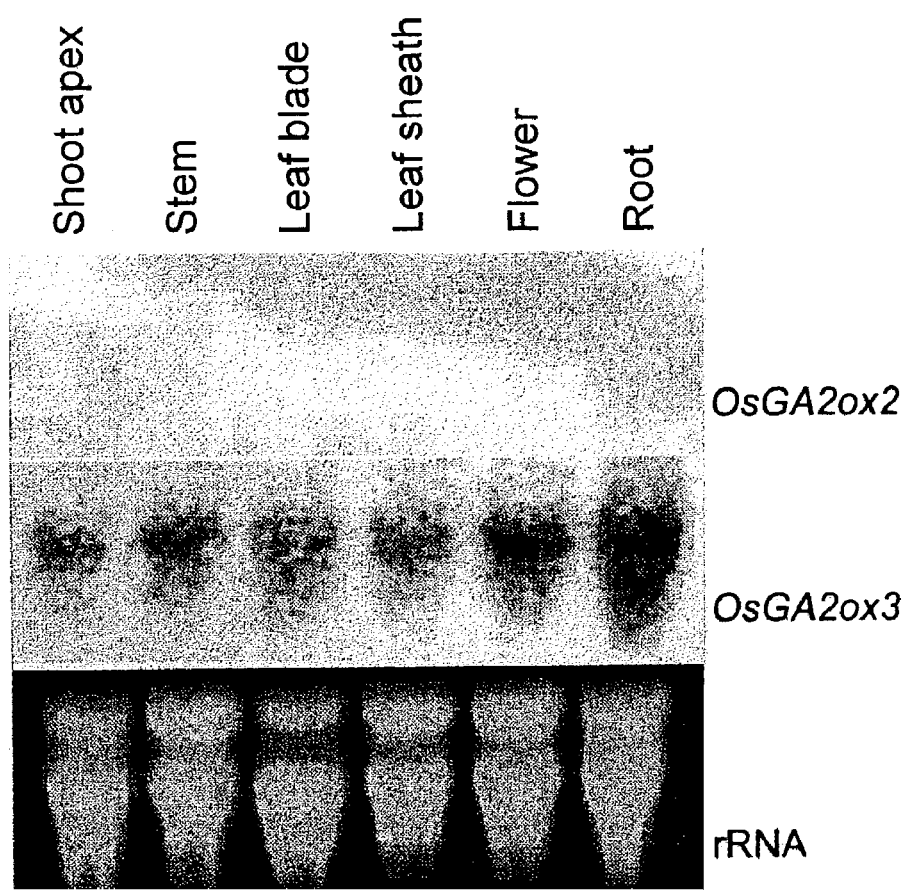
FIG. 3 is a photograph showing the expression of OsGA2ox2 and OsGA2ox3 in various organs of wild type rice. Total RNAs (10 μg) were isolated from growing shoot apexes, stems, leaf blades, leaf sheaths, flowers, and roots to use for Northern blotting, and the blots were hybridized with $^{32}$P-labeled cDNAs for OsGA2ox2 (upper panel) and OsGA2ox3 (middle panel). The bottom panel shows an image of an agarose gel stained with ethidium bromide.

RNA gel blot analysis was performed to investigate the expression patterns of OsGA2ox2 and OsGA2ox3 in various organs of rice (FIG. 3). Transcript of OsGA2ox3 was detected at a high level in stems, flowers, and roots, and at a relatively low level in the growing shoot apex, leaf blades, and leaf sheathes. No transcript of OsGA2ox2 was detected in any tissues by RNA gel blot analysis. Similar results were obtained by gel blot analysis of RT-PCR products. It was confirmed that the expression pattern of OsGA2ox3 is very similar to that of OsGA3ox2, which encodes GA3β-hydroxylase in growing rice tissues (Itoh, H. et al., Proc. Natl. Acad. Sci. USA 98(15): 8909–14, 2001).

EXAMPLE 3

For functional analysis of OsGA2ox3, a recombinant protein was prepared, and incubated with the substrates, tritium-labeled $GA_{20}$, $GA_{29}$, and $GA_1$ as previously described (Sakamoto, T. et al., Plant Physiol., 125(3): 1508–16, (2001)). Full scan GC-MS analysis revealed that $GA_1$ is converted into the corresponding 2β-hydroxide $GA_8$ (Table 1).

TABLE 1

| Substrate | Product[a] | KRI | Characteristic ions m/z (% relative level) |
|---|---|---|---|
| [$^2H_2$]$GA_1$ | [$^2H_2$]$GA_8$ | 2821 | 596(100), 581(7), 537(8), 450(23), 209(61) |
| [$^2H_2$]$GA_{20}$ | [$^2H_2$]$GA_{29}$-catabolite | 2688 | 448(100), 419(52), 389(35), 329(14), 240(23) |
| [$^2H_2$]$GA_{29}$ | [$^2H_2$]$GA_{29}$-catabolite | 2687 | 448(100), 419(68), 389(31), 329(15), 240(23) |

[a]Identification of the products was conducted by GC-MS based on the full scan mass spectrum of KRI and methyl-ester-trimethylsilylether derivative.

Figure 4:
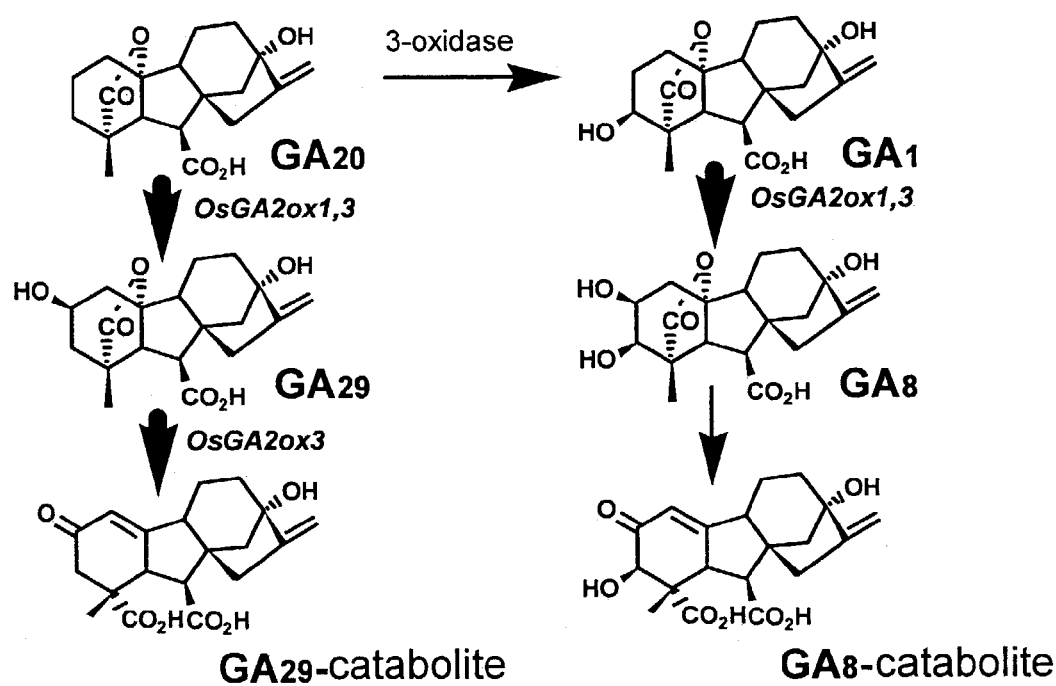
FIG. 4 shows the synthetic and metabolic pathway of $GA_1$ in rice. The bold arrows show the steps catalyzed by rice GA2-oxidase.

However, $GA_{20}$ was metabolized to a $GA_{29}$-catabolite. Furthermore, the metabolism of $GA_{29}$ to a $GA_{29}$-catabolite was confirmed by metabolism experiments. The results showed that OsGA2ox3 catalyzes a two-step oxidation, i.e. metabolism of $GA_{20}$ to $GA_{29}$ and $GA_{29}$ to $GA_{29}$-catabolite (FIG. 4).

EXAMPLE 4

Figure 5:
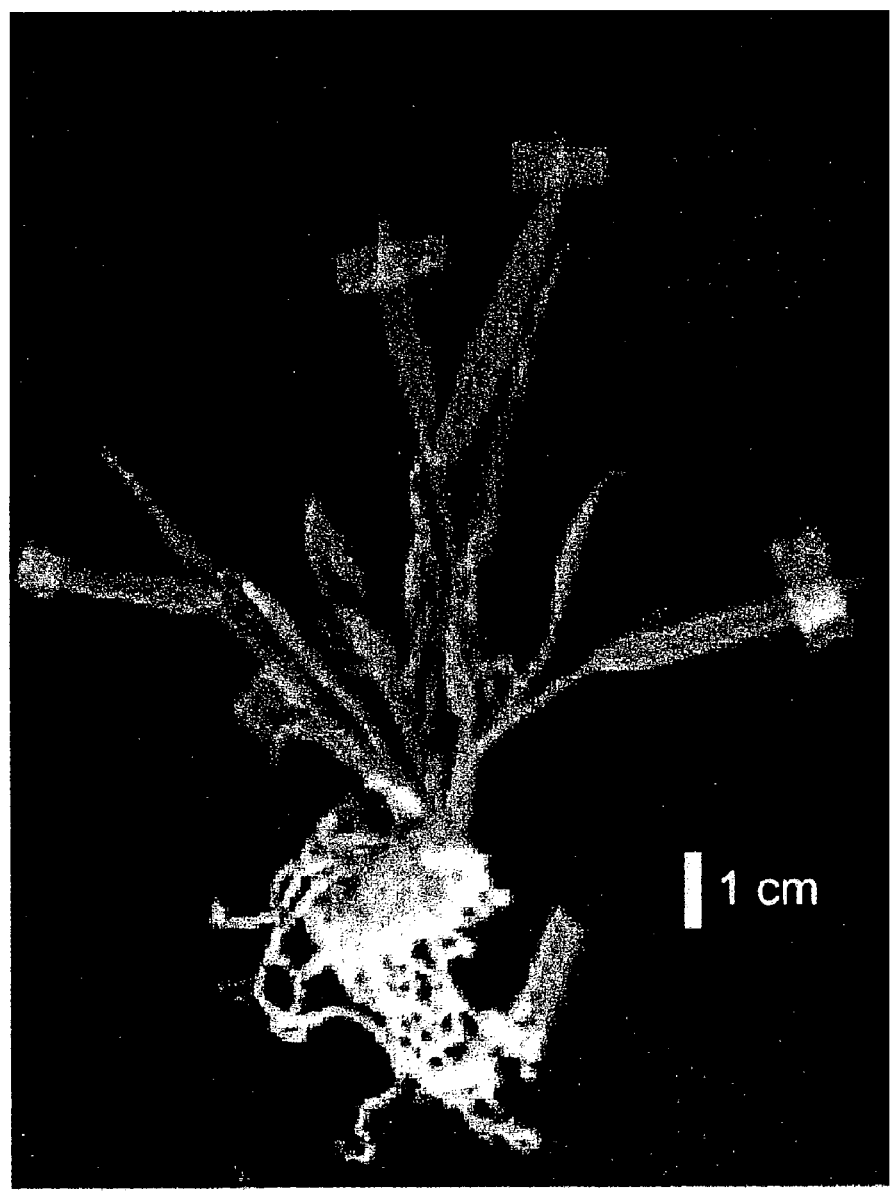
FIG. 5 is a photograph showing a transgenic rice plant overexpressing the OsGA2ox3 cDNA. The scale bar represents 1 cm.

To test the activity of the OsGA2ox3 gene product in vivo, the full-length OsGA2ox3 cDNA was fused to the rice actin promoter and introduced into wild type rice by Agrobacterium-mediated gene transfer. All the transgenic plants from 27 independent lines showed extreme dwarf phenotypes (FIG. 5). Leaf blades of these plants were dark green, and they were shorter and wider than those of the wild type plants. All of these phenotypes are typical for GA-deficient dwarf rice plants. Wild type plants flowered about three months after seeding, but the mutant plants did not flower even after four months following seeding.

EXAMPLE 5

Figure 6:
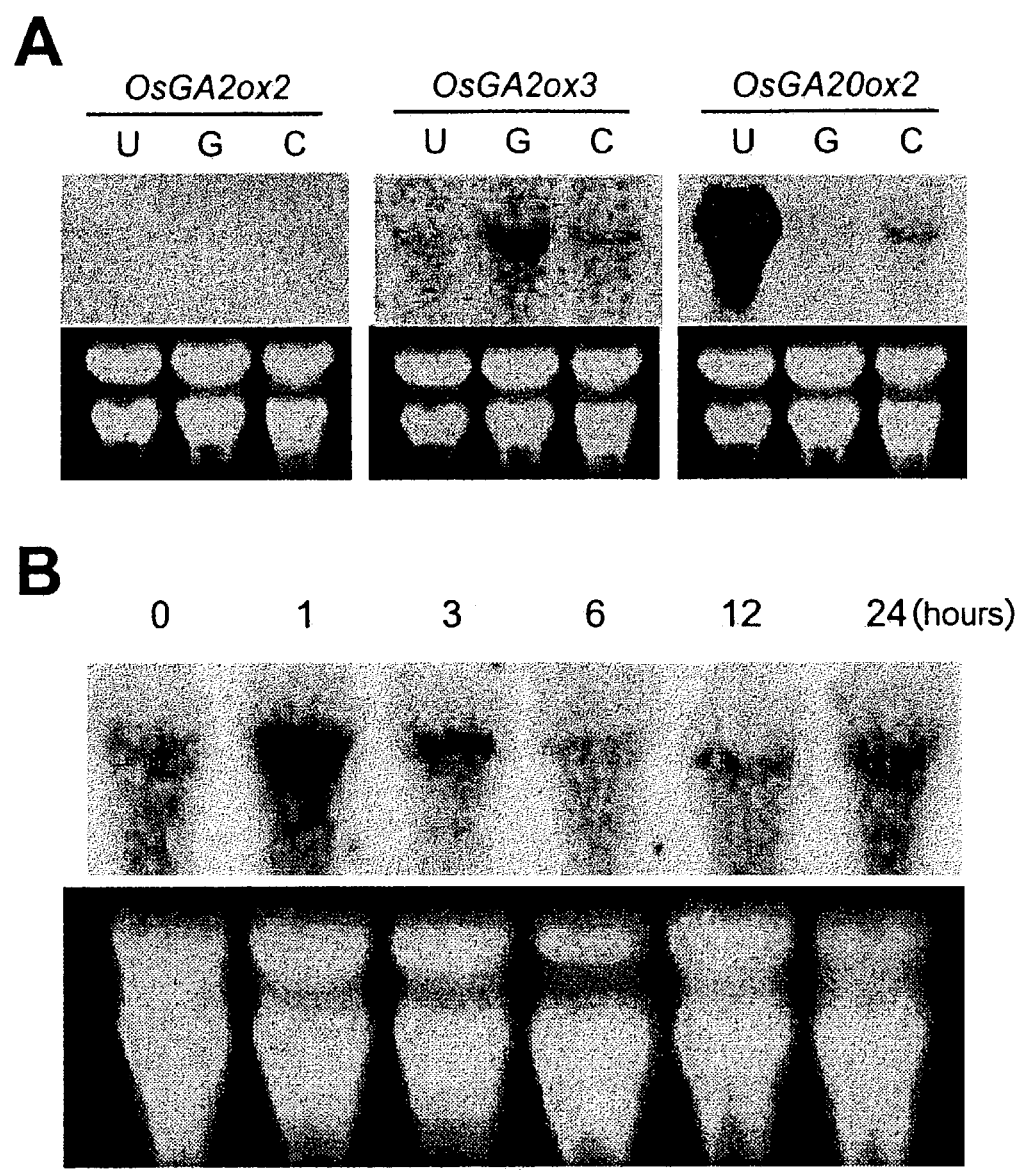
FIG. 6 shows photographs depicting the influence of GA and uniconazole on the transcriptional levels of rice genes involved in GA biosynthesis and GA metabolism. A: (Top panel): total RNAs (10 μg) were isolated from untreated (C) wild-type rice seedlings or those treated with 10 μM $GA_3$ (G) and 10 μM uniconazole (U) to use for Northern blotting, and the blots were hybridized with $^{32}$P-labeled cDNAs for OsGA2ox2, OsGA2ox3 and OsGA20ox2. (Bottom panel): images of agarose gel stained with ethidium bromide. B: Photographs showing changes in the transcription of OsGA2ox3 after application of 10 M $GA_3$. (Top panel) total RNAs (10 μg) were prepared 0, 1, 3, 6, 12, and 24 hours after the application to use for blotting. (Bottom panel) an image of an agarose gel stained with ethidium bromide.

The influence of uniconazole, a suppressor of $GA_3$ and GA biosyntheses, on the transcriptional level of OsGA2ox2 and OsGA2ox3 (FIG. 6A) was examined. Transcription level of OsGA2ox3 was increased by $GA_3$ treatment, but decreased by uniconazole (FIG. 6A) treatment. On the contrary, the influence of $GA_3$ and uniconazole on the transcriptional level of the OsGA20ox1 gene, which encodes the synthase GA20-oxidase, was completely reversed. Transcription of the OsGA2ox3 gene was not detected even after $GA_3$ treatment. Further studies revealed that the transcription level of the OsGA2ox3 gene was increased for one hour after $GA_3$ treatment, but, after six hours, the level was decreased to a level that was even lower than the transcription level observed before $GA_3$ treatment (FIG. 6B).

The present inventors isolated two novel genes encoding GA2-oxidases, OsGA2ox2 and OsGA2ox3, from rice. OsGA2ox3 was confirmed to inactivate both $GA_1$ and its direct precursor $GA_{20}$ (FIG. 4). Thus, there are at least two active GA2-oxidase genes, OsGA2ox1 and OsGA2ox3 in rice. Whereas OsGA2ox3 is GA-responsive, OsGA2ox1 is not. The product of OsGA2ox3 gene, unlike that of OsGA2ox1 gene, catalyzes the multi-step oxidation of $GA_{20}$. The expression of OsGA2ox3 was observed in all the tissues examined, and was regulated by the concentrations of biologically active GAs in a feedforward manner. Feedforward regulation of GA2-oxidase genes has been already reported for AtGA2ox1 and AtGA2ox2 (Thomas, S. G. et al., Proc. Natl. Acad. Sci. USA 96:4698–4703, 1999).

In conclusion, OsGA2ox3 was suggested to have a role in the homeostatic regulation of the concentrations of biologically active GAs in rice. On the other hand, OsGA2ox1 is thought to have a particular role in events such as regulation of the growth of the apical meristem (Sakamoto, T. et al., Plant Physiol. 125(3): 1508–16, (2001)). It is particularly notable that there are two rice GA3β-hydroxylase genes (OsGA3ox1 and OsGA3ox2): OsGA3ox2 is under feedback regulation by biologically active GA concentration, but OsGA3ox1 is not (Itoh, H. et al., Proc. Natl. Acad. Sci. USA 98(15): 8909–14, 2001). Thus, it is contemplated that $GA_1$ concentration is maintained at an appropriate level through homeostatic regulation of OsGA3ox2 (activation) and OsGA2ox3 (inactivation). This mechanism should be important for regulating the growth of stems and leaves of rice plants.

Equivalents

Those skilled in the art will recognize, or be able to ascertain using no more than routine experimentation, many equivalents to the specific embodiments of the invention described herein. Such equivalents are intended to be encompassed by the following claims. The contents of all references, patents and patent applications cited throughout this application are hereby incorporated by reference.

What is claimed is:

1. An isolated DNA encoding a plant protein having gibberellin 2 oxidation activity, wherein said DNA is selected from the group consisting of:
   a) a DNA encoding a protein consisting of the amino acid sequence as set forth in SEQ ID NO: 4;
   b) a DNA consisting of the coding region of the nucleotide sequence as set forth in SEQ ID NO: 3;
   c) a DNA encoding a protein consisting of the amino acid sequence as set forth in SEQ ID NO: 4, wherein up to ten amino acid residues are substituted, deleted, added, and/or inserted; and
   d) a DNA hybridizing to the DNA consisting of the nucleotide sequence as set forth in SEQ ID NO: 3 under stringent conditions and at least 95% identical to the entirety of SEQ ID NO: 3.

2. The DNA according to claim 1, wherein said protein encoded by said DNA catalyzes the conversion of gibberellin $A_{20}$ to gibberellin $A_{29l}$ which is further metabolized to gibberellin $A_{29}$-catabolite.

3. The DNA according to claim 1, wherein said plant is a monocotyledon.

4. The DNA according to claim 2, wherein said plant is a monocotyledon.

5. A vector comprising an isolated DNA, wherein the DNA encodes a plant protein having gibberellin 2 oxidation activity, wherein said DNA is selected from the group consisting of:
   a) a DNA encoding a protein consisting of the amino acid sequence as set forth in SEQ ID NO: 4;
   b) a DNA consisting of the coding region of the nucleotide sequence as set forth in SEQ ID NO: 3;
   c) a DNA encoding a protein consisting of the amino acid sequence as set forth in SEQ ID NO: 4, wherein up to ten amino acid residues are substituted, deleted, added, and/or inserted; and
   d) a DNA hybridizing to the DNA consisting of the nucleotide sequence as set forth in SEQ ID NO: 3 under stringent conditions and at least 95% identical to the entirety of SEQ ID NO: 3.

6. The vector of claim 5, wherein said protein encoded by said DNA catalyzes the conversion of gibberellin $A_{20}$ to gibberellin $A_{29}$, which is further metabolized to gibberellin $A_{29}$-catabolite.

7. The vector of either claims 5 or 6, wherein said plant is a monocotyledon.

8. A transformed plant cell comprising the DNA according to any one of claims 1 to 4.

9. A transgenic plant comprising the transformed plant cell according to claim 8.

10. A transgenic plant that is an offspring or clone of the transgenic plant according to claim 9, wherein the transgenic plant comprises said DNA.

11. A propagation material obtained from the transgenic plant according to claim 9, wherein the propagation material comprises said DNA.

12. A method of producing a transgenic plant which comprises the steps of
 a) introducing a DNA or a vector consisting DNA into a plant cell, wherein the DNA is selected from the group consisting of:
  i) a DNA encoding a protein consisting of the amino acid sequence as set forth in SEQ ID NO: 4;
  ii) a DNA consisting of the coding region of the nucleotide sequence as set forth in SEQ ID NO: 3;
  iii) a DNA encoding a protein consisting of the amino acid sequence as set forth in SEQ ID NO: 4, wherein up to ten amino acid residues are substituted, deleted, added, and/or inserted; and
  iv) a DNA hybridizing to the DNA consisting of the nucleotide sequence as set forth in SEQ ID NO: 3 under stringent conditions and at least 95% identical to the entirety of SEQ ID NO: 3; and
 b) regenerating a plant from said plant cell.

13. The method according to claim 12, wherein said protein encoded by said DNA catalyzes the conversion of gibberellin $A_{20}$ to gibberellin $A_{29}$, which is further metabolized to gibberellin $A_{29}$-catabolite.

14. The method according to either claims 12 or 13, wherein said plant is a monocotyledon.

15. A plant growth suppressor comprising an isolated DNA according to any one of claims 1 to 4 as an active ingredient.

16. A method of suppressing plant growth, which comprises expressing the isolated DNA according to any one of claims 1 to 4 in plant cells.

17. A propagation material obtained from the transgenic plant according to claim 10, wherein the propagation material comprises said DNA.

* * * * *

UNITED STATES PATENT AND TRADEMARK OFFICE
CERTIFICATE OF CORRECTION

| | |
|---|---|
| PATENT NO. | : 7,154,028 B2 |
| APPLICATION NO. | : 10/392325 |
| DATED | : December 26, 2006 |
| INVENTOR(S) | : Hiroshi Tanaka et al. |

It is certified that error appears in the above-identified patent and that said Letters Patent is hereby corrected as shown below:

In Claim 2, column 27, line 66, replace "$A_{291}$" with --$A_{29}$--

In Claim 12, column 29, line 19, replace "consisting" with --comprising--

Signed and Sealed this

Thirty-first Day of July, 2007

JON W. DUDAS
*Director of the United States Patent and Trademark Office*